(12) United States Patent
Kalergis Parra et al.

(10) Patent No.: US 8,398,993 B2
(45) Date of Patent: Mar. 19, 2013

(54) IMMUNOGENIC FORMULATION

(75) Inventors: Alexis Mikes Kalergis Parra, Santiago (CL); Pablo Alberto Gonzalez Munoz, Santiago (CL); Susan Marcela Bueno Ramirez, Santiago (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 0 days.

(21) Appl. No.: 12/679,091

(22) PCT Filed: Sep. 17, 2008

(86) PCT No.: PCT/US2008/076682
§ 371 (c)(1),
(2), (4) Date: Sep. 3, 2010

(87) PCT Pub. No.: WO2009/039178
PCT Pub. Date: Mar. 26, 2009

(65) Prior Publication Data
US 2011/0200634 A1    Aug. 18, 2011

(30) Foreign Application Priority Data

Sep. 20, 2007 (CL) .................................. 2710-2007

(51) Int. Cl.
*A61K 39/155* (2006.01)
*A61K 39/04* (2006.01)
*A61K 39/02* (2006.01)
(52) U.S. Cl. ............... 424/211.1; 424/184.1; 424/200.1; 424/201.1; 424/234.1; 424/248.1

(58) Field of Classification Search .................... None
See application file for complete search history.

(56) References Cited

U.S. PATENT DOCUMENTS 7,070,786 B2 * 7/2006 Scallon ...................... 424/186.1
2006/0115494 A1 * 6/2006 Sun et al. ................... 424/200.1

* cited by examiner

*Primary Examiner* — Rodney P. Swartz
(74) *Attorney, Agent, or Firm* — Venable LLP; Nancy J. Axelrod; Michael A. Gollin (57) ABSTRACT

The present invention describes an immunogenic formulation to be used in mammals against the respiratory syncytial virus (RSV), consisting in the Calmette-Guérin bacillus (BCG) strain or other attenuated *Mycobacterium* strain that expresses heterologously at least one protein or immunogenic fragment of the RSV subtype A or RSV subtype B strains, originated from proteins NS1, NS2, N, P, M, SH, M2 (ORF1), M2 (ORF2), L, F or G. The genetic material that encodes for these proteins or immunogenic fragments is inserted into the BCG genome or extrachromosomally in one or several copies, which expression is regulated by endogenous or exogenous BCG promoters, either constitutive or inducible. The viral proteins or immunogenic fragments can be expressed by BCG as cytoplasmic-soluble, extracellularly-secreted or cell membrane-bound proteins. The preparation can further contain combinations of previously described formulations. The formulation can be stabilized by freeze-drying (conservation range from 4° C. and 25° C.) or through low temperatures (−80° C.) in a buffered saline solution to be conserved prior to its use.

18 Claims, 5 Drawing Sheets

IMMUNOGENIC FORMULATION

This application is a National Stage Application of PCT/US2008/076682, filed 17 Sep. 2008, which claims benefit of Serial No. 2710-2007, filed 20 Sep. 2007 in Chile and which applications are incorporated herein by reference. To the extent appropriate, a claim of priority is made to each of the above disclosed applications.

FIELD OF THE INVENTION

The present invention is directed to the field of immunology and is particularly directed to an immunogenic formulation to be used to prepare a vaccine against the respiratory syncytial virus (RSV). This formulation comprises at least one recombinant attenuated live *Mycobacterium* strain, preferably the Calmette-Guérin bacillus strain (BCG), recombinant for one or more RSV immunogenic proteins or fragments, stabilized in a buffered saline solution.

BRIEF DESCRIPTION OF THE INVENTION

The present invention comprises an immunogenic formulation that induces protection against the infection caused by the respiratory syncytial virus (RSV) and/or attenuates the pathology caused by this virus in mammals. The immunogenic formulation of the present invention can be used to prepare vaccines and contains colony forming units (CFU) (for example, ranging from $1 \times 10^4$-$1 \times 10^9$ CFU per dose) of live recombinant attenuated *Mycobacterium* strains, preferably the Calmette-Guérin bacillus strain (BCG), which express one or more RSV immunogenic proteins or fragments recombinantly or heterologously and are conserved by freeze-drying (within a temperature range from 4° C. to 25° C.) or in a stabilizing saline solution (within a temperature range from −80° C. to 4° C.) prior to their use. For example, the immunogenic formulation resuspended in diluted Sauton SSI solution (125 µg $MgSO_4$, 125 µg $K_2HPO_4$, 1 mg L-asparagine, 12.5 µg ferric ammonia citrate, 18.4 mg 85% glycerol, 0.5 mg citric acid, 1 ml $H_2O$ for injection) and conserved at 4° C.; the immunogenic formulation in PBS (137 mM NaCl, 2.7 mM KCl; 4.3 mM $Na_2HPO_4$; 1.47 mM $KH_2PO_4$, pH 7.4) supplemented with 0.02% Tween 80 and 20% glycerol and conserved at −80° C.; or the immunogenic formulation resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), freeze-dried and conserved at a temperature range from 4° C. and 25° C.

The recombinant attenuated *Mycobacterium* bacteria of the immunogenic formulation of the present invention containing one or more genes that encode for at least one protein or immunogenic fragment from RSV subtypes RSV A or RSV B or both. These RSV proteins or immunogenic fragments correspond to proteins NS1, NS2, N, P, M, SH, M2 (ORF1), M2 (ORF2), L, F or G from RSV and are inserted into the bacterial genome or into extrachromosomal plasmids in one or more copies, and their expression is controlled by endogenous or exogenous BCG promoters, either constitutive or inducible. These RSV proteins or immunogenic fragments can be expressed by BCG or other attenuated *Mycobacterium* strains as cytoplasmic-soluble, extracellularly-secreted or cell membrane-bound proteins.

The immunogenic formulation disclosed in the present invention can be used together with immunogenic formulations that contain other attenuated *Mycobacterium* or BCG strains, which are different in that they express different immunogenic RSV proteins, and/or in the gene location (genome-inserted or extrachromosomal), and/or in the copy number of the protein gene, and/or the promoter that induces protein expression, and/or the destination of the RSV protein or immunogenic fragments (cytoplasmic-soluble, extracellularly-secreted or membrane-bound proteins).

The attenuated *Mycobacterium* bacteria of the immunogenic formulation previously described comes from a *Mycobacterium* bacteria culture in exponential-growth or stationary phase, corresponding to an optical density at 600 nm ranging from 0.5 and 1.5, in buffered saline solution (PBS-0.02% Tween 80 or diluted Sauton SSI solution).

The immunogenic formulation previously described can be administered to an individual in a subcutaneous, percutaneous or subdermic form together with a buffered saline or physiological solution such as, e.g., diluted Sauton SSI solution (125 µg $MgSO_4$, 125 µg $K_2HPO_4$, 1 mg L-asparagine, 12.5 µg ferric ammonia citrate, 18.4 mg 85% glycerol, 0.5 mg citric acid, 1 ml $H_2O$ for injection).

The immunogenic formulation previously described can be used to vaccinate individuals that have or have not being previously in contact with the respiratory syncytial virus, with the aim of conferring immunity against RSV.

BACKGROUND OF THE INVENTION

The Respiratory Syncytial Virus (RSV) is the main causing agent of acute respiratory tract infections in young children worldwide. According to WHO, this virus infects 64 million people yearly, 160.000 of which die (www.who.int). The infection by this virus causes a broad range of clinical symptoms that can be as slight as rhinitis or much more severe such as pneumonia or bronchiolitis, the worst cases being observed in unweaned babies, premature babies, children with congenital cardiopathies and immunodepressed children (1-3).

The infection caused by this virus is utterly frequent and recurrent, since practically 100% of the children younger than 3 years-old have had at least one episode of RSV infection (4). As this infection does not leave a complete immunological memory (5), reinfection is frequent, being less severe as the patient's age increases.

The health situation caused by RSV infection generates a high economical impact for the affected countries. Studies carried out in developed countries estimate that the cost of this infection is over 3.000 euros per patient (6), with a highest limit reaching up to 8.400 euros (6).

The RSV is a negative, unsegmented, single-strand RNA virus with a lipid coat that belongs to the paramyxoviridae virus family, genus pneumovirus (reviewed in (7)). RSV possesses a genome with about 15 kb that encodes for a total of 11 proteins. Five of these proteins have structural functions, corresponding to the transmembrane F, G and SH proteins, the nucleocapsid N protein and the matrix M protein. The other four proteins, M2-1, M2-2, P and L are involved in viral replication and transcription. The remaining two proteins, called NS1 and NS2, are non-structural proteins and they seem to be involved in virulence (8).

The RSV that infects humans has different strains or subgroups, being subgroups A and B those that predominate in the population (reviewed in (9)). The main antigen difference between the subgroups is related to protein G, which only conserves 40-44% of its amino acids between different subgroups (9).

The first vaccine against RSV was tested in the 1960's and comprised a formalin-inactivated complete virus (RSV-FI)

that was administered intramuscularly in the presence of alum adjuvant (10). Contrarily to the expected result, this immunization caused a much more severe respiratory case after RSV infection in the vaccinated children, which led to hospitalization of 80% of them and two deaths (11). The respiratory-pulmonary clinical symptoms presented by the vaccinated children were characterized by an unusual eosinophil and neutrophil infiltration together with a high titer of complement-fixing antibodies (11). The analysis of the affected pulmonary tissues of the children vaccinated with RSV-FI that died due to RSV infection showed complement deposition, immune complexes and eosinophil presence in peribronchial regions (12). Together with this, animal studies demonstrate that vaccination with RSV-FI produces a Th2-type immune response, based on T CD4+ lymphocytes, that possesses the same characteristics than those observed in animals that have been immunized with protein G (13) or that receive T CD4+ lymphocytes specific for this protein prior to RSV infection. For this reason, to formulate an effective and safe vaccine against RSV it has been necessary to study thoroughly the immune response generated against the different proteins of this virus, with the aim of identifying those that are able to induce a Th1-type immune response based on interferon-gamma (IFN-γ)-producing and cytotoxic T-lymphocytes.

The current research on vaccines against RSV has been focused on the analysis and development of viral subunits, such as proteins F (14), M2 (15) and also certain conserved protein G segments (16). On the other hand, the production of vaccines based on mutant RSV virus strains, such as those sensitive to temperature (17), having deletions in certain genes (18) or recombinant for cytokines such as GM-CSF (19), has also been studied. Some of these vaccines have been tested in Phase-I and II clinical trials, with variable results (20-22). Other putative vaccine against RSV is represented by the group of vaccines based on proteins F and G, which are administered with adjuvants such as ISCOMs. The immunization with this type of vaccines produces an increased eosinophil infiltration in the pulmonary tissue when a new viral infection develops (23), which increases the damage to the pulmonary tissue.

The immune system of a young child is characterized by developing preferentially Th2-type immune responses, which is possibly caused by the immaturity of the immune system during the first six months of life (24, 25). Nevertheless, if adequately stimulated, the immune system can present a Th1-type response (26). To formulate an effective and safe vaccine against RSV it has been necessary to study thoroughly the immune response generated against the different proteins of this virus, with the aim of identifying those that are able to induce a Th1-type immune response based on cytotoxic T-lymphocytes. The use of bacterial vectors for heterologous expression of viral antigens has the advantage that these bacterial vectors can be used as attenuated living vectors, as they have intact invasion abilities and are recognized as non-pathogenic. An additional advantage of certain bacterial vectors used to express heterologous antigens is their known ability to induce Th1-type immunity (27, 28) which is very attractive for the case of the development of vaccines against RSV (29). The Calmette-Guérin bacillus (BCG) is an attenuated *Mycobacterium bovis* strain that is used as a vaccine against *Mycobacterium tuberculosis* in newborns. From the approval of BCG as a vaccine against tuberculosis, this has been administered to more than 3.3 trillion people worldwide. Its massive use has been facilitated by many advantageous characteristics of these bacteria, such as their high thermostability in freeze-dried form. Moreover, the immunization of newborn children with this bacterium is risk-free and only produces minimal side effects. BCG is highly immunogenic and only one dose is able to generate an immune response that is maintained for long terms. Importantly, BCG induces a potent Th1-type immune response both in adults and children (30). This phenomenon is evidenced in newborns by the cell-type immune response generated against antigens of *M. tuberculosis* (PPD), which is able to survive during extended periods (30).

Up to this date, several bacterial, parasite and viral antigens have been successfully expressed in this bacterial system, which were demonstrated to induce humoral and cellular immunity against these antigens when evaluated in animal models (31, 32). Moreover, BCG has the particularity of not being neutralized by antibodies present in maternal milk, and therefore it can be used as immunity inducer in unweaned babies. The present invention relates to an immunological formulation that comprises one or more attenuated *Mycobacterium* bacterial strains, preferably the BCG strain, recombinant for RSV proteins, and can be used to prepare vaccines against this virus.

Figure 2:
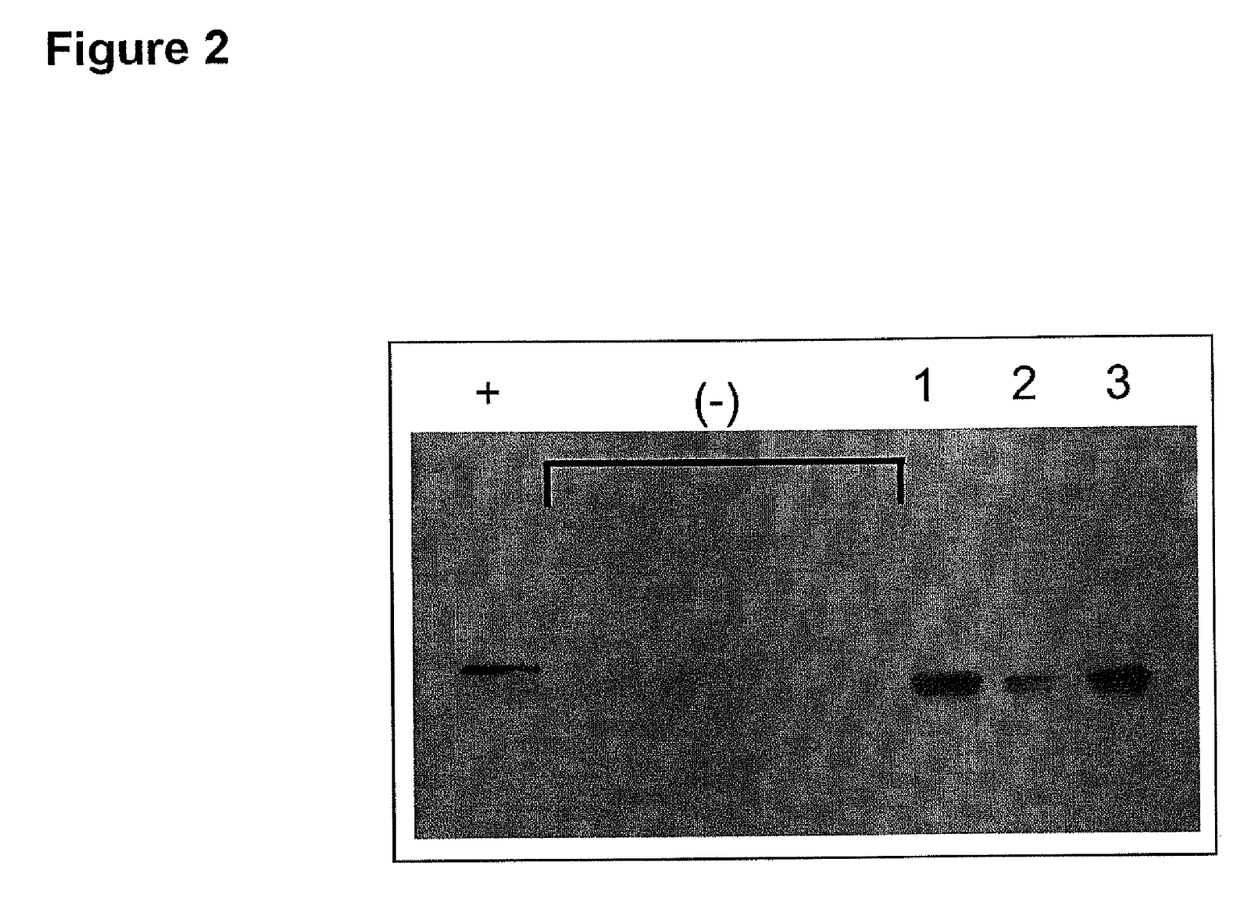

This formulation is directed to avoid or attenuate the pulmonary damage caused by a RSV infection, thanks to the generation of an efficient immune response that is favorable to eliminate the virus. Since attenuated *Mycobacterium* strains such as BCG are potent Th1-type immune response inducers, the immune response induced by BCG strains recombinant for RSV favors a protection against infections caused by this virus.

BRIEF DESCRIPTION OF THE FIGURES

FIG. 1 is an immunoblot (Western Blot) assay to assess the expression of protein N from RSV in a BCG strain. This attenuated *Mycobacterium* strain contains a single copy of the protein N gene from RSV inserted into its genome, under the control of the constitutive hsp60 promoter and is expressed by the bacteria in a constitutive form. The protein is obtained from the soluble fraction of a total bacterial extract. A protein extraction was performed on multiple BCG clones transformed with the plasmid pMV361-N and preserved in a PBS (137 mM NaCl; 2.7 mM KCl; 4.3 mM $Na_2HPO_4$; 1.47 mM $KH_2PO_4$, pH 7.4)-0.05% Tween 80-20% glycerol solution at −80° C. A rabbit polyclonal antibody raised against protein N from RSV was used to detect the presence of the protein; (+) is a positive assay control, consisting in 0.25 μg of recombinant protein N; (−) is a negative assay control, consisting in 25 μg of proteins from a BCG strain that had not been transformed with pMV361-N; lanes 1-5 are 25 μg of proteins from BCG clones transformed with pMV361-N. It can be concluded that protein N from RSV is successfully expressed in BCG when the gene is inserted into its genome under the control of a constitutive promoter.

FIG. 2 is an immunoblot (Western Blot) assay to assess the expression of protein M2 from RSV in a BCG strain conserved in a PBS (137 mM NaCl; 2.7 mM KCl; 4.3 mM $Na_2HPO_4$; 1.47 mM $KH_2PO_4$, pH 7.4)-0.05% Tween 80-20% glycerol solution at −80° C. This attenuated *Mycobacterium* BCG strain contains a single copy of the protein M2 gene from RSV inserted into its genome, under the control of the constitutive hsp60 promoter and is expressed by the bacteria in a constitutive form. The protein is obtained from the soluble fraction of a total bacterial extract. A protein extraction was performed from BCG clones transformed with the plasmid pMV361-M2. A rabbit polyclonal antibody raised against protein M2 from RSV was used to detect the presence of the protein; (+) is a positive assay control, consisting in 25

μg of a total lisate of HEp-2 cells infected by RSV; (−) is a negative assay control, consisting in 25 μg of proteins from a BCG strain that had not been transformed with pMV361-M2; lanes 1-3 are 25 μg of protein from BCG clones transformed with pMV361-M2. It can be concluded that protein M2 from RSV is successfully expressed in BCG when the gene is inserted into its genome and is under the control of a constitutive promoter.

Figure 3:
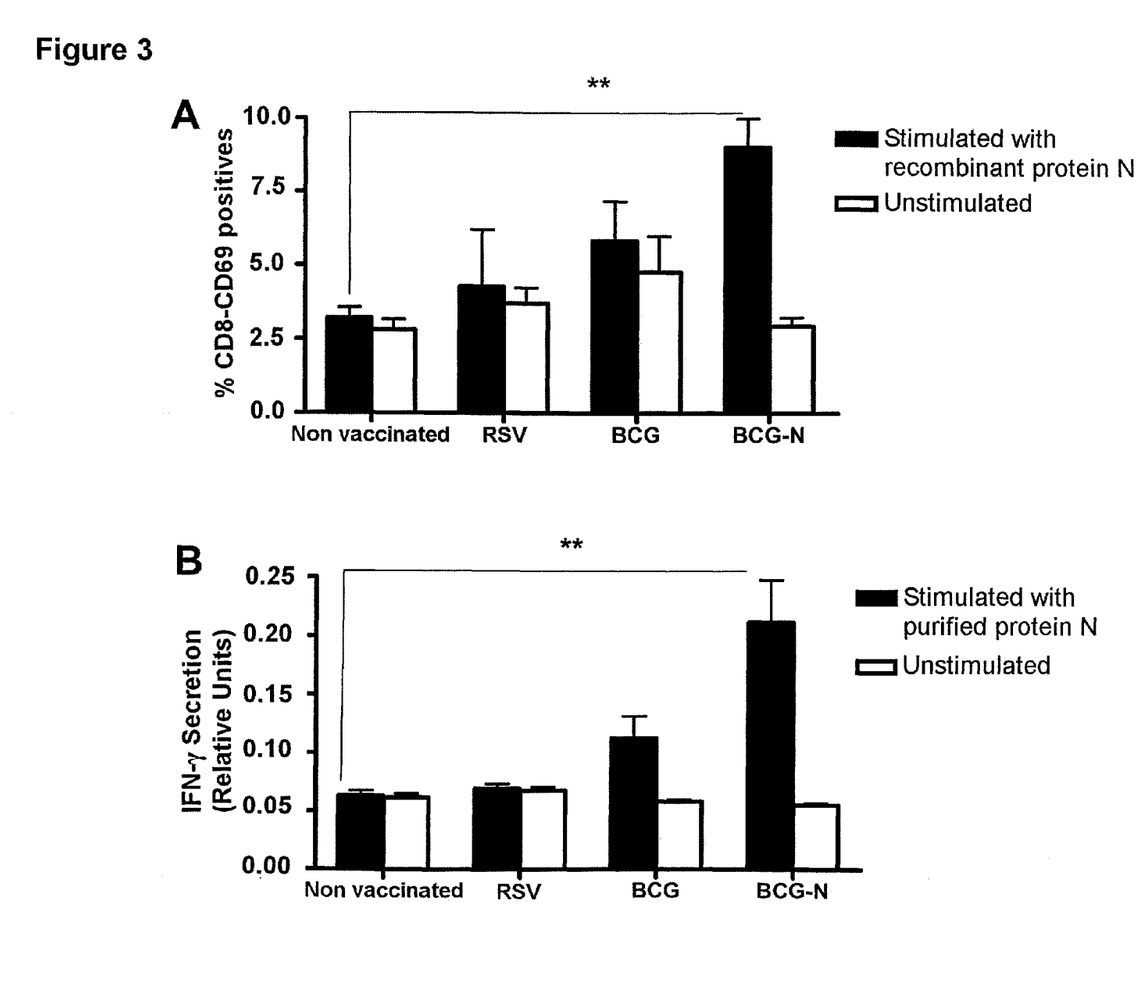

FIG. 3 shows the percentage of CD8+-CD69+ cells (A) and IFN-γ secretion (B) (33) of spleen cells from BALB/c mice immunized with BCG that expresses protein N in saline solution (PBS: 137 mM NaCl; 2.7 mM KCl; 4.3 mM $Na_2HPO_4$; 1.47 mM 1($KH_2PO_4$, 0.02% Tween 80, pH 7.4, at 4° C.). $5\times10^5$ cells from the spleen of animals that were not immunized, or were immunized with $1\times10^7$ PFU of RSV, immunized with BCG ($1\times10^8$ CFU/mouse in PBS: 137 mM NaCl; 2.7 mM KCl; 4.3 mM $Na_2HPO_4$; 1.47 mM $KH_2PO_4$, 0.02% Tween 80, pH 7.4, 4° C.) or immunized with BCG recombinant for protein N from RSV ($1\times10^8$ CFU/mouse in PBS: 137 mM NaCl; 2.7 mM KCl; 4.3 mM $Na_2HPO_4$; 1.47 mM $KH_2PO_4$, 0.02% Tween 80, pH 7.4, 4° C.), were stimulated for 72 hrs with 0.5 μM protein N from RSV. Subsequently, the percentage of cells positive for CD8 and CD69 markers was determined by flow cytometry (A). Cell supernatants were subjected to ELISA to detect the presence of secreted IFN-γ (33). **, p value of 0.002, Student's t-Test. It can be concluded that the BCG strain recombinant for protein N from RSV causes a favorable T lymphocyte response in mice immunized with this immunogenic formulation. As a response to a challenge with recombinant protein N, these T lymphocytes are activated, express activation markers on their surface (CD69+) and secrete IFN-γinto the extracellular medium.

FIG. 4 shows a body weight variation curve for BALB/c mice immunized with a BCG strain recombinant for protein N from RSV ($1\times10^8$ CFU/mouse, in PBS: 137 mM NaCl; 2.7 mM KCl; 4.3 mM $Na_2HPO_4$; 1.47 mM $KH_2PO_4$, 0.02% Tween 80, pH 7.4, 4° C.) or with a BCG strain recombinant for protein M2 from RSV ($1\times10^8$ CFU/mouse, in PBS: 137 mM NaCl; 2.7 mM KCl; 4.3 mM $Na_2HPO_4$; 1.47 mM $KH_2PO_4$, 0.02% Tween 80, pH 7.4, 4° C.). BALB/c mice that were not vaccinated (■), or were immunized with $1\times10^7$ plaque forming units (PFU) of RSV inactivated by ultraviolet light (UV lamp, 312 nm, 8 watts power) by 20 minutes (RSV-UV) (▲), or immunized with a wild-type (WT) BCG strain that does not express RSV proteins (▼) ($1\times10^8$ CFU/mouse, in PBS: 137 mM NaCl; 2.7 mM KCl; 4.3 mM $Na_2HPO_4$; 1.47 mM $KH_2PO_4$, 0.02% Tween 80, pH 7.4, 4° C.), or were immunized with a BCG strain transformed with pMV361-N (◆) ($1\times10^8$ CFU/mouse, in PBS: 137 mM NaCl; 2.7 mM KCl; 4.3 mM $Na_2HPO_4$; 1.47 mM $KH_2PO_4$, 0.02% Tween 80, pH 7.4, 4° C.) or were immunized with a BCG strain transformed with pMV361-M2 (Δ) ($1\times10^8$ CFU/mouse, in PBS: 137 mM NaCl; 2.7 mM KCl; 4.3 mM $Na_2HPO_4$; 1.47 mM $KH_2PO_4$, 0.02% Tween 80, pH 7.4, 4° C.), were infected intranasally with $1\times10^7$ PFU of RSV, strain 13018-8. As a control, a group of mice not vaccinated and not infected was included (●). The variation in body weight with respect to day 0 was registered daily for 4 days. **, p value of 0.002, Student's t-Test. It can be concluded that mice immunization with a BCG strain recombinant for protein N or protein M2 from RSV induces a favorable response against RSV infection, since the body weight of these mice does not vary significantly when compared with that of non vaccinated mice, in which body weight decreasing is observed.

FIG. 5 shows representative lung histological cuts from BALB/c mice immunized and infected intranasally with $1\times10^7$ PFU of RSV, strain 13018-8. (A-B), lungs of uninfected mice; (C-D), lungs of non-immunized mice infected with RSV; (E-F), lungs of mice immunized against RSV and infected with RSV; (G-H), mice immunized with BCG recombinant for protein N from RSV ($1\times10^8$ CFU/mouse in PBS: 137 mM NaCl; 2.7 mM KCl; 4.3 mM $Na_2HPO_4$; 1.47 mM $KH_2PO_4$, 0.02% Tween 80, pH 7.4, at 4° C.) and (I-J) mice immunized with BCG recombinant for protein M2 from RSV ($1\times10^8$ CFU/mouse in PBS: 137 mM NaCl; 2.7 mM KCl; 4.3 mM $Na_2HPO_4$; 1.47 mM $KH_2PO_4$, 0.02% Tween 80, pH 7.4, at 4° C.). The right panels correspond to 40× amplified microphotographs and the left panels correspond to 100× amplified microphotographs, marked with a polyclonal antibody anti-RSV-HRP (USBiologicals) that shows the presence of viral proteins in epithelial pulmonary cells. The infected pulmonary cells are darker (indicated by arrows). It can be concluded that mice immunized with the BCG strain recombinant for protein N from RSV develop a favorable T lymphocyte response against infection by RSV. After a RSV infection, a lower cell infiltration can be observed in lungs from vaccinated mice in comparison with non-immunized animals. Moreover, a lower number of virus-infected pulmonary cells in mice vaccinated with the BCG strain recombinant for protein N from RSV was observed in comparison with the controls.

DETAILED DESCRIPTION OF THE INVENTION

The present invention comprises an immunogenic formulation that can be used to prepare a vaccine that induces protection against the infection caused by the respiratory syncytial virus (RSV) and/or attenuates the pathology caused by this virus in mammals. The immunogenic formulation of the present invention can be used to prepare vaccines and contains colony forming units (CFU) (for example, ranging from $1\times10^4$-$1\times10^9$ CFU per dose) of living recombinant attenuated *Mycobacterium* strains, preferably the Calmette-Guérin bacillus strain (BCG) (for example, the Pasteur or Danish BCG strains (34), American Type Culture Collection, www.atcc.org, ATCC numbers 35734 and 35733 respectively), which express one or more RSV immunogenic proteins or fragments recombinantly or heterologously and are conserved by freeze-drying or in a stabilizing saline prior to their use. For example, the immunogenic formulation conserved in diluted Sauton SSI solution (125 μg $MgSO_4$, 125 μg $K_2HPO_4$, 1 mg L-asparagine, 12.5 μg ferric ammonia citrate, 18.4 mg 85% glycerol, 0.5 mg citric acid, in 1 ml $H_2O$) at 4° C.; the immunogenic formulation conserved in PBS (137 mM NaCl, 2.7 mM KCl; 4.3 mM $Na_2HPO_4$; 1.47 mM $KH_2PO_4$, pH 7.4) supplemented with 0.02% Tween 80 and 20% glycerol, at −80° C.; or the immunogenic formulation resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), freeze-dried and conserved at a temperature range from 4° C. and 25° C.

The recombinant attenuated *Mycobacterium* bacteria of the immunogenic formulation of the present invention contain genes that encode for at least one protein or immunogenic fragment from RSV subtypes RSV A or RSV B or both. The genome of the respiratory syncytial virus has been previously described in the GenBank data base, with access numbers gI-9629367 and gI-9629198. These immunogenic proteins or fragments from RSV correspond to proteins NS1, NS2, N, P, M, SH, M2 (ORF1), M2 (ORF2), L, F or G from RSV, and are contained in the plasmid pMV361 (37), which is incorporated into the bacteria through electrotransformation according to previously described techniques (35), and is incorporated in turn into the bacterial genome by the action of mycobacteriophage integrases (36). These genes can also be found in extrachromosomal plasmids such as e.g. pMV261 (37), which is incorporated into *Mycobacterium* through electrotransformation, according to previously described techniques (35) and is maintained extrachromosomally in bacteria (36). These genes can be present as a single or multiple copies, and its expression is commanded by endogenous BCG promoters (e.g. the hsp60 gene promoter from BCG), either constitutive or inducible (e.g. the hsp60 gene promoter and the acr gene promoter, respectively). These RSV immunogenic proteins or fragments can be expressed by BCG or other attenuated *Mycobacterium* strains, in soluble-cytoplasmic, extracellularly-secreted or membrane-bound form, thanks to the fusion of the respiratory syncytial virus genes or immunogenic fragments thereof with DNA sequences that encode for peptides that function as protein destination signals toward the different bacterial compartments (for example, the N-terminal sequence of the alpha-antigen gene for extracellular secretion and the N-terminal sequence of the 19-kDa protein gene for membrane bound proteins).

The immunogenic formulation disclosed in the present invention can be used together with immunogenic formulations that contain one or more attenuated *Mycobacterium* or BCG strains, which are different in that they express different immunogenic RSV proteins, and/or in the gene location (genome-inserted or extrachromosomal), and/or in the copy number of the protein gene, and/or the promoter that induces protein expression, and/or the destination of the RSV protein or immunogenic fragments (cytoplasmic-soluble, extracellularly-secreted or membrane-bound proteins).

The attenuated *Mycobacterium* bacteria of the formerly described immunogenic formulation come from a *Mycobacterium* bacterial culture (for example, at 37° C. in culture medium supplemented with 4.9 g/L of Middlebrock 7H9 culture medium, Difco, catalog number 0713-01-7, 1× enrichment OADC Beckton Dickinson medium, catalog number 212351; 5% glycerol and 0.05% Tween 80) in exponential growth or stationary phase, at an optical density at 600 nm ranging from 0.5 to 1.5, in buffered saline solution (PBS-0.02% Tween 80, or diluted Sauton SSI solution).

The immunogenic formulation previously described can be administered to an individual in a subcutaneous, percutaneous or subdermic form together with a buffered saline or physiological solution, e.g., diluted Sauton SSI solution (125 μg MgSO$_4$, 125 μg K$_2$HPO$_4$, 1 mg L-asparagine, 12.5 μg ferric ammonia citrate, 18.4 mg 85% glycerol, 0.5 mg citric acid, 1 ml H$_2$O for injection).

The immunogenic formulation previously described can be used to vaccinate individuals that have or have not being previously in contact with the respiratory syncytial virus, with the aim of conferring immunity against this virus or attenuate the pathology caused by it.

EXAMPLES

The following examples of the generation and use of BCG strains recombinant for proteins from the respiratory syncytial virus (RSV) are only illustrative and are not intended to limit the production or application scope of this invention. Even though in the following descriptions specific terms are used, their use is only descriptive and not limiting.

Example I

Immunogenic formulation consisting of 10$^8$ bacteria of the BCG Danish strain recombinant for the N gene from RSV subtype A. The gene is inserted into the bacterial genome, under regulation by the endogenous constitutive hsp60 promoter from BCG and the protein is expressed cytoplasmically. The immunogenic formulation can be contained in a diluted Sauton SSI solution (125 μg MgSO$_4$, 125 μg K$_2$HPO$_4$, 1 mg L-asparagine, 12.5 μg ferric ammonia citrate, 18.4 mg 85% glycerol, 0.5 mg citric acid, 1 ml H$_2$O) at −80° C. The formulation can also be contained in a PBS (137 mM NaCl; 2.7 mM KCl; 4.3 mM Na$_2$HPO$_4$; 1.47 mM KH$_2$PO$_4$, pH 7.4) solution, supplemented with 20% glycerol and 0.02% Tween 80 at a final concentration of 10$^8$ bacteria per 100 μl and conserved at −80° C. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried and conserved at 25° C.

Figure 1:
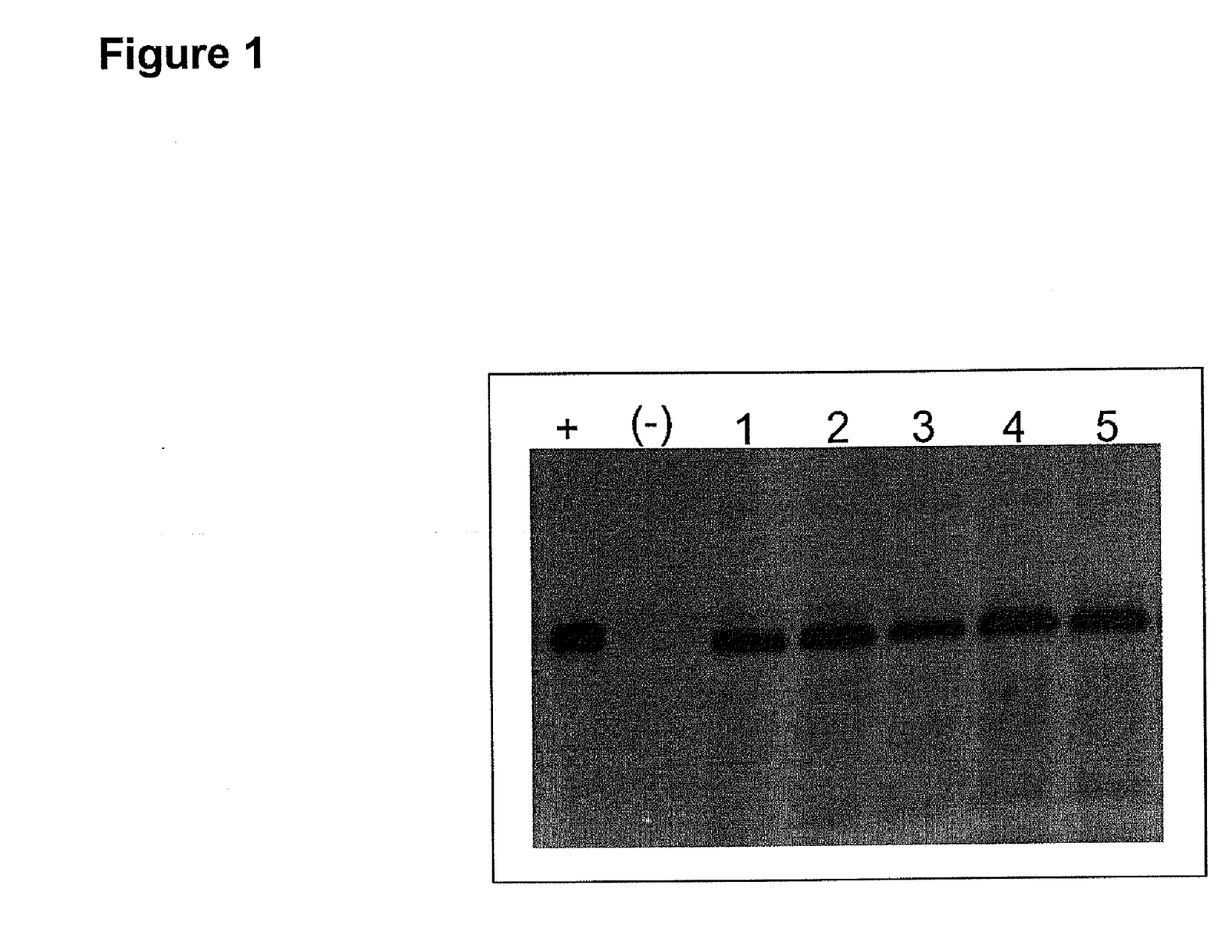
Figure 4:
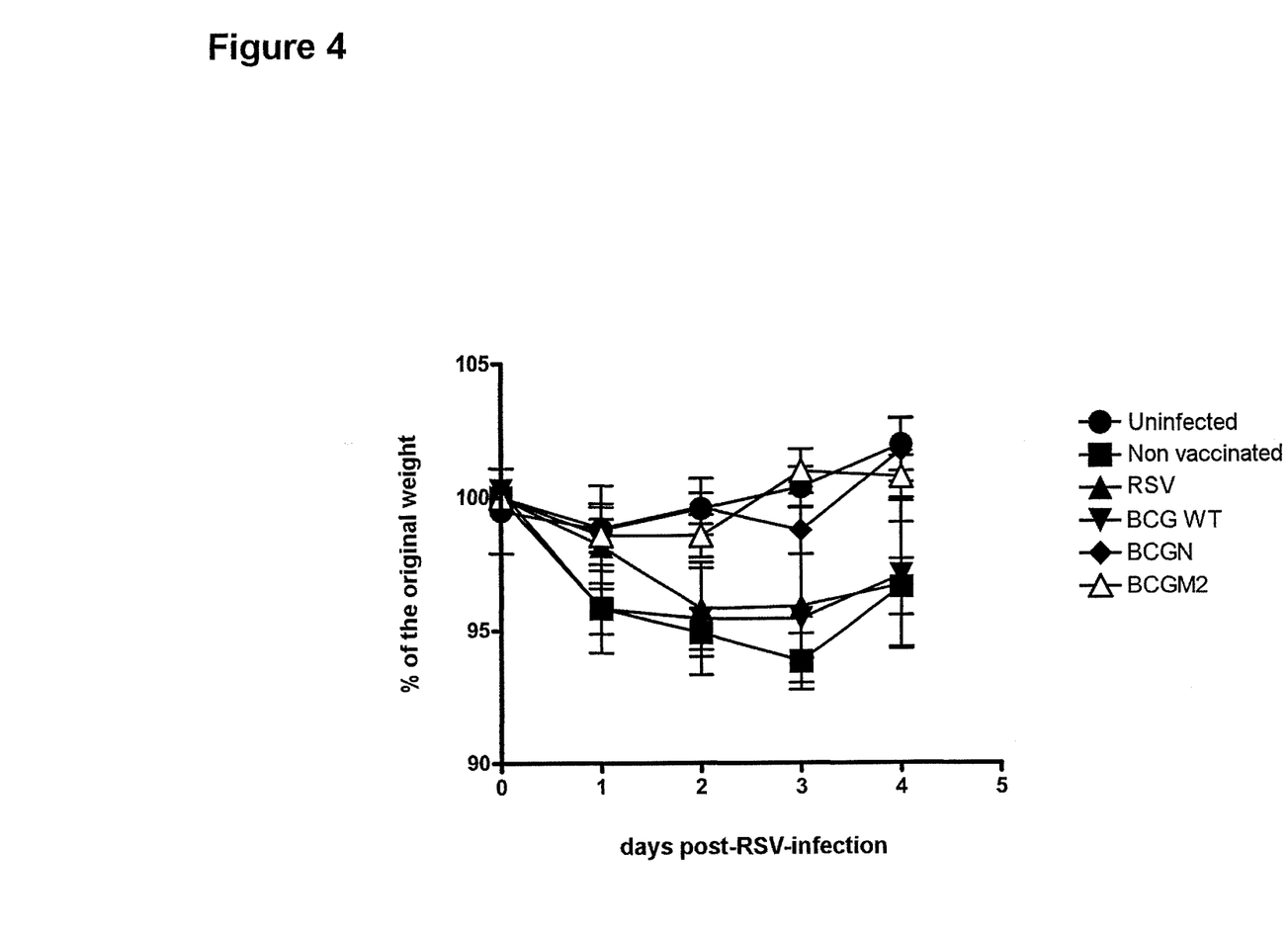
Figure 5:
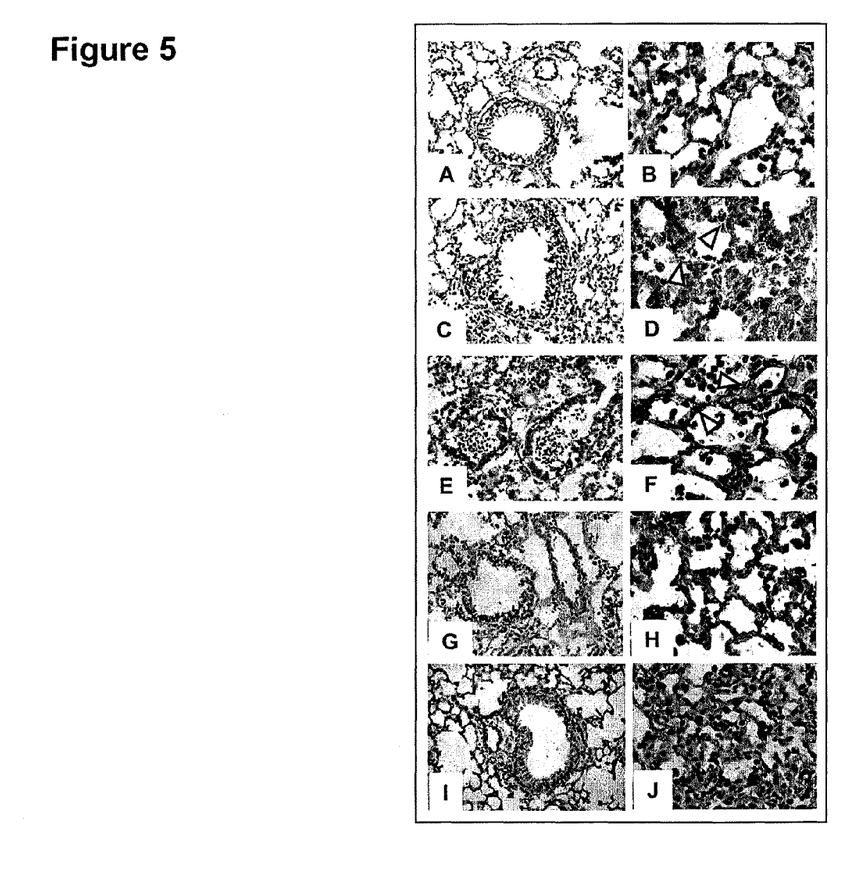

The BCG Danish strain (American Type Culture Collection, www.atcc.org, ATCC number 35733) was transformed by electrotransformation (35) with the pMV361/N plasmid, derived from the pMV361 plasmid (37), which is inserted once into the bacterial genome. This plasmid contains the gene that encodes for the protein N from RSV subtype A, which is expressed under regulation of the endogenous and constitutive promoter of the hsp60 gene from BCG. The resulting recombinant colonies were grown (at 37° C. in supplemented Middlebrock 7H9 culture medium) up to OD$_{600\,nm}$=1, centrifuged at 4,000 rpm for 20 min (Eppendorf rotor model 5702/R A-4-38) and resuspended in PBS (137 mM NaCl; 2.7 mM KCl; 4.3 mM Na$_2$HPO$_4$; 1.47 mM KH$_2$PO$_4$, pH 7.4) solution, supplemented with 20% glycerol and 0.02% Tween 80 at a final concentration of 10$^8$ bacteria per 100 μl and conserved at −80° C. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried and conserved at 25° C. Through a Western Blot assay using antibodies raised against the protein N from RSV, it can be observed that this BCG strain recombinantly expresses the protein N from RSV subtype A in the cytoplasm (FIG. 1). The immunization of BALB/c mice with the described formulation used as a vaccine, confers protection to these animals against an intranasal infection with 10$^7$ plaque forming units of RSV subtype A (FIGS. 4 and 5). This immunogenic formulation is able to confer immunity against the protein N from RSV subtypes A and B.

Example II

Immunogenic formulation consisting of 5×10$^7$ bacteria of the BCG Danish strain recombinant for the N gene from RSV subtype A and 5×10$^7$ bacteria of the BCG Danish strain recombinant for the M2 gene from RSV subtype A. In each of the bacteria that comprise the immunogenic formulation, RSV genes are inserted in a single copy into the bacterial genome, under regulation by the endogenous constitutive hsp60 promoter from BCG and the protein is expressed cytoplasmically. The immunogenic formulation can be preserved in PBS (137 mM NaCl; 2.7 mM KCl; 4.3 mM Na$_2$HPO$_4$; 1.47 mM KH$_2$PO$_4$, pH 7.4), supplemented with 20% glycerol and 0.02% Tween 80 at a final concentration of 10$^8$ bacteria per 100 μl and conserved at −20° C. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried and conserved at 4° C.

The BCG Danish (American Type Culture Collection, www.atcc.org, ATCC number 35733), strain was transformed by electrotransformation (35) with the pMV361/N or pMV361/M2 plasmids that are derived from the pMV361 plasmid (37), which are inserted once into the bacterial genome. These plasmids contain the protein N and M2 genes from RSV subtype A, respectively, under the control of the constitutive hsp60 gene promoter from BCG. The resulting recombinant colonies were grown (at 37° C. in supplemented Middlebrock 7H9 culture medium) up to $OD600_{nm}=1$, centrifuged at 4,000 rpm for 20 mM (Eppendorf rotor model 5702/R A-4-38) and resuspended in PBS (137 mM NaCl; 2.7 mM KCl; 4.3 mM $Na_2HPO_4$; 1.47 mM $KH_2PO_4$, pH 7.4) solution, supplemented with 20% glycerol and 0.02% Tween 80 at a final concentration of 107 bacteria per 100 µl and conserved at –20° C. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried and conserved at 4° C. Through a Western Blot assay using antibodies raised against the proteins N and M2 from RSV, it can be observed that these BCG Danish strains recombinantly express the proteins N and M2 from RSV subtype A (FIGS. 1 and 2). This immunogenic formulation is able to confer simultaneous immunity against the proteins N and M2 from RSV subtypes A and B.

Example III

Immunogenic formulation consisting of $10^6$ bacteria of the BCG Pasteur strain recombinant for a segment of the protein F from RSV subtype B. The gene is found extrachromosomally in bacteria in multiple copies (2-4 copies per bacterium) and encodes for a fragment of the protein F from RSV subtype B (segment from the amino acid 5 to the amino acid 200). The expression of this gene is under the control of the endogenous constitutive promoter of the gene that encodes for the alpha-antigen protein (85 kDa) from BCG. Moreover, the protein encoded by this gene possesses the peptide signal HMKKRGLTVAVAGAAILVAGLSGCSSNK-STTGSGETTTTAAGTTASPGG (SEQ ID NO: 1) at its'N-terminal end, which belongs to the 19 kDa protein of BCG and induces its expression at the bacterial membrane. The immunogenic formulation is preserved in PBS (137 mM NaCl; 2.7 mM KCl; 4.3 mM $Na_2HPO_4$; 1.47 mM $KH_2PO_4$, pH 7.4), supplemented with 0.02% Tween 80 and 20% glycerol at –80° C. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried and conserved at 4° C.

The BCG Pasteur strain (American Type Culture Collection, www.atcc.org, ATCC number 35734), was transformed by electrotransformation (35) with the $pMV261/F_{5-200}$ plasmid, derived from the pMV261 plasmid (37), which resides extrachromosomally in multiple copies inside the bacteria. This plasmid encodes for a fragment of the F gene from RSV subtype B (segment from the amino acid 5 to the amino acid 200) fused at its N-terminal end with the peptide signal: HMKKRGLTVAVAGAAILVAGLSGCSSNK-STTGSGETTTTAAGTTASPGG (SEQ ID NO:1) of the 19 kDa protein from BCG, which induces its expression on the bacterial membrane. The expression of this gene is under the control of the endogenous constitutive promoter of the gene that encodes for the alpha-antigen protein (85 kDa) from BCG. The resulting recombinant colonies were grown up to $OD_{600}$ nm=1, at 37° C. in supplemented Middlebrock 7H9 culture medium, centrifuged at 4,000 rpm for 20 min (Eppendorf rotor model 5702/R A-4-38) and resuspended in PBS (137 mM NaCl; 2.7 mM KCl; 4.3 mM $Na_2HPO_4$; 1.47 mM $KH_2PO_4$, pH 7.4), supplemented with 0.02% Tween 80 and 20% glycerol at a final concentration of $10^6$ bacteria per 100 µl. Similarly, the strains can be resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), and then freeze-dried in aliquots containing $10^6$ bacteria each and conserved at 4° C. This immunogenic formulation is able to confer immunity against the protein F from RSV subtypes A and B.

Example IV

Immunogenic formulation consisting of $10^5$ bacteria of the BCG Danish strain recombinant simultaneously for the N and M2 genes from RSV subtype A. The N gene is inserted into the bacterial genome, under regulation by the endogenous constitutive hsp60 promoter from BCG and the protein is expressed cytoplasmically. The M2 gene is found extrachromosomally in bacteria in multiple copies (2-4 copies per bacterium) under the control of the endogenous constitutive promoter of the gene that encodes for the alpha-antigen protein (85 kDa) from BCG. The protein encoded by the M2 gene has at its N/terminal end the peptide signal: HMKKRGLTVAVAGAAILVAGLSGCSSNK-STTGSGETTTTAAGTTASPGG (SEQ ID NO:1) of the 19 kDa protein from BCG, which induces its expression on the bacterial membrane. The immunogenic formulation is preserved at 4° C., freeze-dried from bacteria resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), freeze-dried and conserved at 4° C. Similarly, the strains can be preserved in a PBS (137 mM NaCl; 2.7 mM KCl; 4.3 mM $Na_2HPO_4$; 1.47 mM $KH_2PO_4$, pH 7.4) solution, supplemented with 0.02% Tween 80 and 20% glycerol at a final concentration of $10^5$ bacteria per 100 µl.

The BCG Danish strain (American Type Culture Collection, www.atcc.org, ATCC number 35733), was transformed by electrotransformation (35) with the pMV361/N plasmid, derived from the pMV361 plasmid (37), which inserted once into the bacterial genome. This plasmid contains the gene that encodes for the protein N from RSV subtype A, which is expressed under regulation of the endogenous and constitutive promoter of the hsp60 gene from BCG. After assessing that the resulting BCG strain is recombinant for the protein N from RSV, this was transformed by electrotransformation (35) with the pMV206/M2 plasmid, derived from the pMV206 plasmid (37), which resides extrachromosomally in multiple copies inside the bacteria. The protein encoded by the M2 gene possesses the peptide signal HMKKRGLTVAVAGAAILVAGLSGCSSNK-STTGSGETTTTAAGTTASPGG (SEQ ID NO: 1) at its N-terminal end, which belongs to the 19 kDa protein of BCG and induces its expression at the bacterial membrane. The resulting recombinant colonies were grown up to $OD_{600\,nm}=1$, at 37° C. in supplemented Middlebrook 7H9 culture medium, centrifuged at 4,000 rpm for 20 min (Eppendorf rotor model 5702/8 A-4-38) and resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), at a final concentration of $10^5$ bacteria per 1 ml. Finally, 1-ml aliquots with $10^5$ bacteria were freeze-dried and conserved at 4° C. Similarly, the strains can be preserved in a PBS (137 mM NaCl; 2.7 mM KCl; 4.3 mM $Na_2HPO_4$; 1.47 mM $KH_2PO_4$, pH 7.4) solution, supplemented with 0.02% Tween 80 and 20% glycerol at a final concentration of $10^5$ bacteria per 100 µl. This immunogenic formulation is able to confer immunity against the proteins N and M2 from RSV subtypes A and B.

Example V

Immunogenic formulation consisting of $10^4$ bacteria of the BCG Danish strain recombinant for the N gene from RSV subtype A. The gene is inserted in a single copy into the bacterial genome under regulation of the acr inducible endogenous promoter from BCG, which is active in response to nitric oxide, low oxygen concentrations and stationary growth phase. The protein expression is cytoplasmic. The immunogenic formulation is freeze-dried in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water), conserved at 25° C. in a diluted Sauton SSI solution (125 µg $MgSO_4$, 125 µg $K_2HPO_4$, 1 mg L-asparagine, 12.5 µg ferric ammonia citrate, 18.4 mg 85% glycerol, 0.5 mg citric acid, in 1 ml $H_2O$). Similarly, the strains can be preserved in a PBS (137 mM NaCl; 2.7 mM KCl; 4.3 mM $Na_2HPO_4$; 1.47 mM $KH_2PO_4$, pH 7.4) solution, supplemented with 0.02% Tween 80 and 20% glycerol at a final concentration of 104 bacteria per 100 µl.

The BCG Danish strain (American Type Culture Collection, www.atcc.org, ATCC number 35733), was transformed by electrotransformation (35) with the pMV361$_{Pacr}$/N plasmid, derived from the pMV361 plasmid (37), which is inserted once into the bacterial genome. This plasmid contains the gene that encodes for the protein N from RSV subtype A, which is expressed under regulation of the endogenous and inducible acr promoter from BCG. The resulting recombinant colonies were grown (at 37° C. in supplemented Middlebrook 7H9 culture medium) up to $OD_{600\,nm}=1$, centrifuged at 4,000 rpm for 20 min (Eppendorf rotor model 5702/R A-4-38) and resuspended in a 25% by volume lactose solution and Proskauer and Beck Medium supplemented with glucose and Tween 80 (PBGT: 0.5 g asparagine; 5.0 g potassium dihydrogen phosphate; 1.5 g magnesium citrate; 0.5 g potassium sulfate; 0.5 ml Tween 80 and 10.0 g glucose per liter of distilled water). Finally, 1-ml aliquots with 104 bacteria were freeze-dried and conserved at 25° C. Similarly, the strains can be preserved in a PBS (137 mM NaCl; 2.7 mM KCl; 4.3 mM $Na_2HPO_4$; 1.47 mM $KH_2PO_4$, pH 7.4) solution, supplemented with 0.02% Tween 80 and 20% glycerol at a final concentration of $10^8$ bacteria per 100 µl. This immunogenic formulation is able to confer immunity against the protein N from RSV subtypes A and B.

Example VI

Immunogenic formulation consisting of $10^9$ bacteria of the BCG Danish strain recombinant for the N gene from RSV subtype A. The gene is inserted into the bacterial genome, under regulation by the exogenous T7-phage promoter for constitutive expression in BCG strains that co-express T7-phage polymerase. The protein expression is cytoplasmic. The immunogenic formulation is contained in a diluted Sauton SSI solution (125 µg $MgSO_4$, 125 µg $K_2HPO_4$, 1 mg L-asparagine, 12.5 µg ferric ammonia citrate, 18.4 mg 85% glycerol, 0.5 mg citric acid in 1 ml $H_2O$) and was conserved at −20° C. or may be freeze-dried and conserved at 4° C. Similarly, the strains can be preserved in a PBS (137 mM NaCl; 2.7 mM KCl; 4.3 mM $Na_2HPO_4$; 1.47 mM $KH_2PO_4$, pH 7.4) solution, supplemented with 0.02% Tween 80 and 20% glycerol at a final concentration of $10^9$ bacteria per 100 µl.

The BCG Danish (American Type Culture Collection, www.atcc.org, ATCC number 35733), strain was transformed by electrotransformation (35) with the pMV361$_{PT7}$/N plasmid, derived from the pMV361 plasmid (37), which is inserted once into the bacterial genome. This plasmid contains the gene that encodes for the protein N from RSV subtype A, which is expressed under regulation of the T7 promoter activated by the expression of the T7-phage polymerase (39). The resulting BCG strain was transformed by electrotransformation (35) with the pMV261$_{Amp}$/PolT7 plasmid, derived from the pMV261 plasmid (37), which resides extrachromosomally in multiple copies inside the bacteria. In this plasmid, the resistance against the antibiotic kanamycin (40) has been replaced by resistance against hygromycin (Hygr). The T7 polymerase from the T7 phage is under control of the constitutive promoter of the hsp60 from BCG. The resulting recombinant colonies were grown at 37° C. in supplemented Middlebrock 7H9 culture medium up to $OD_{600\,nm}=1$, centrifuged at 4,000 rpm for 20 min (Eppendorf rotor model 5702/R A-4-38) and resuspended in diluted Sauton SSI solution (125 µg $MgSO_4$, 125 µg $K_2HPO_4$, 1 mg L-asparagine, 12.5 µg ferric ammonia citrate, 18.4 mg 85% glycerol, 0.5 mg citric acid in 1 ml $H_2O$) and conserved at −80° C. This immunogenic formulation is able to confer immunity against the protein N from RSV subtypes A and B.

The former examples are extensive to immunological formulations that contain a recombinant attenuated *Mycobacterium* strain that expresses proteins NS2, N, P, M, SH, M2 (ORF1), M2 (ORF2), L, F or G from RSV, as well as all the combinations thereof. Similarly, the examples are extensive to immunological formulations that contain one or several recombinant attenuated *Mycobacterium* strains; Wherein said recombinant bacteria contain protein or immunogenic fragment genes from RSV that are inserted into the bacterial genome or in extrachromosomal plasmids, in one or more copies, and their expression is under the control of endogenous or exogenous constitutive or inducible promoters, being expressed as soluble-cytoplasmic, extracellularly-secreted or membrane-bound proteins.

All publications referred to herein (including all publications listed in the references section) are hereby incorporated by reference. Where the reference is cited to provide information about a method or a material as described herein, the portion of the reference referring to that method or material is specifically incorporated herein.

REFERENCES

1. Cabalka, A. K. 2004. Physiologic risk factors for respiratory viral infections and immunoprophylaxis for respira- 1. tory syncytial virus in young children with congenital heart disease. In *Pediatr Infect Dis J*, Vol. 23, p. S41.
2. Carpenter, T. C., and K. R. Stenmark. 2004. Predisposition of infants with chronic lung disease to respiratory syncytial virus-induced respiratory failure: a vascular hypothesis. In *Pediatr Infect Dis J*, Vol. 23, p. S33.
3. Weisman, L. E. 2003. Populations at risk for developing respiratory syncytial virus and risk factors for respiratory syncytial virus severity: infants with predisposing conditions. In *Pediatr Infect Dis J*, Vol. 22, p. S33.
4. Anderson, J. J., J. A. Harrop, H. Peers, T. Turnbull, G. L. Toms, and R. Scott. 1991. Recognition of respiratory syncytial (RS) virus proteins by human and BALB/C CD4+ lymphocytes. In *J Med Virol*, Vol. 35, p. 165.
5. Hall, C. B., E. E. Walsh, C. E. Long, and K. C. Schnabel. 1991. Immunity to and frequency of reinfection with respiratory syncytial virus. In *J Infect Dis*, Vol. 163, p. 693.
6. Rietveld, E., H. C. De Jonge, J. J. Polder, Y. Vergouwe, H. J. Veeze, H. A. Moll, and E. W. Steyerberg. 2004. Anticipated costs of hospitalization for respiratory syncytial virus infection in young children at risk. In *Pediatr Infect Dis J*, Vol. 23, p. 523.
7. Wertz, G. W., and R. M. Moudy. 2004. Antigenic and genetic variation in human respiratory syncytial virus. In *Pediatr Infect Dis J*, Vol. 23, p. S19.
8. Spann, K. M., K. C. Tran, B. Chi, R. L. Rabin, and P. L. Collins. 2004. Suppression of the induction of alpha, beta, and lambda interferons by the NS1 and NS2 proteins of human respiratory syncytial virus in human epithelial cells and macrophages [corrected]. In *J Virol*, Vol. 78, p. 4363.
9. Sullender, W. M. 2000. Respiratory syncytial virus genetic and antigenic diversity. In *Clin Microbiol Rev*, Vol. 13, p. 1.
10. Potash, L., A. A. Tytell, B. H. Sweet, R. A. Machlowitz, J. Stokes, Jr., R. E. Weibel, A. F. Woodhour, and M. R. Hilleman. 1966. Respiratory virus vaccines. I. Respiratory syncytial and parainfluenza virus vaccines. In *Am Rev Respir Dis*, Vol. 93, p. 536.
11. Kim, H. W., J. G. Canchola, C. D. Brandt, G. Pyles, R. M. Chanock, K. Jensen, and R. H. Parrott. 1969. Respiratory syncytial virus disease in infants despite prior administration of antigenic inactivated vaccine. In *Am J Epidemiol*, Vol. 89, p. 422.
12. Polack, F. P., M. N. Teng, P. L. Collins, G. A. Prince, M. Exner, H. Regele, D. D. Lirman, R. Rabold, S. J. Hoffman, C. L. Karp, S. R. Kleeberger, M. Wills-Karp, and R. A. Karron. 2002. A role for immune complexes in enhanced respiratory syncytial virus disease. In *J Exp Med*, Vol. 196, p. 859.
13. Srikiatkhachorn, A., and T. J. Braciale. 1997. Virus-specific memory and effector T lymphocytes exhibit different cytokine responses to antigens during experimental murine respiratory syncytial virus infection. In *J Virol*, Vol. 71, p. 678.
14. Munoz, F. M., P. A. Piedra, and W. P. Glezen. 2003. Safety and immunogenicity of respiratory syncytial virus purified fusion protein-2 vaccine in pregnant women. In *Vaccine*, Vol. 21, p. 3465.
15. Jin, H., X. Cheng, H. Z. Zhou, S. Li, and A. Seddiqui. 2000. Respiratory syncytial virus that lacks open reading frame 2 of the M2 gene (M2-2) has altered growth characteristics and is attenuated in rodents. In *J Virol*, Vol. 74, p. 74.
16. Power, U. F., H. Plotnicky-Gilquin, L. Goetsch, T. Champion, A. Beck, J. F. Haeuw, T. N. Nguyen, J. Y. Bonnefoy, and N. Corvaia. 2001. Identification and characterisation of multiple linear B cell protectopes in the respiratory syncytial virus G protein. In *Vaccine*, Vol. 19, p. 2345.
17. Juhasz, K., S. S. Whitehead, P. T. Bui, J. M. Biggs, J. E. Crowe, C. A. Boulanger, P. L. Collins, and B. R. Murphy. 1997. The temperature-sensitive (ts) phenotype of a cold-passaged (cp) live attenuated respiratory syncytial virus vaccine candidate, designated cpts530, results from a single amino acid substitution in the L protein. In *J Virol*, Vol. 71, p. 5814.
18. Whitehead, S. S., A. Bukreyev, M. N. Teng, C. Y. Firestone, M. St Claire, W. R. Elkins, P. L. Collins, and B. R. Murphy. 1999. Recombinant respiratory syncytial virus bearing a deletion of either the NS2 or SH gene is attenuated in chimpanzees. In *J Virol*, Vol. 73, p. 3438.
19. Bukreyev, A., I. M. Belyakov, J. A. Berzofsky, B. R. Murphy, and P. L. Collins. 2001. Granulocyte-macrophage colony-stimulating factor expressed by recombinant respiratory syncytial virus attenuates viral replication and increases the level of pulmonary antigen-presenting cells. In *J Virol*, Vol. 75, p. 12128.
20. Karron, R. A., P. F. Wright, R. B. Belshe, B. Thumar, R. Casey, F. Newman, F. P. Polack, V. B. Randolph, A. Deatly, J. Hackell, W. Gruber, B. R. Murphy, and P. L. Collins. 2005. Identification of a recombinant live attenuated respiratory syncytial virus vaccine candidate that is highly attenuated in infants. In *J Infect Dis*, Vol. 191, p. 1093.
21. Belshe, R. B., F. K. Newman, E. L. Anderson, P. F. Wright, R. A. Karron, S. Tollefson, F. W. Henderson, H. C. Meissner, S. Madhi, D. Roberton, H. Marshall, R. Loh, P. Sly, B. Murphy, J. M. Tatem, V. Randolph, J. Hackell, W. Gruber, and T. F. Tsai. 2004. Evaluation of combined live, attenuated respiratory syncytial virus and parainfluenza 3 virus vaccines in infants and young children. In *J Infect Dis*, Vol. 190, p. 2096.
22. Polack, F. P., and R. A. Karron. 2004. The future of respiratory syncytial virus vaccine development. In *Pediatr Infect Dis J*, Vol. 23, p. S65.
23. Chen, M., K. F. Hu, B. Rozell, C. Orvell, B. Morein, and P. Liljestrom. 2002. Vaccination with recombinant alphavirus or immune-stimulating complex antigen against respiratory syncytial virus. In *J Immunol*, Vol. 169, p. 3208.
24. Barrios, C., P. Brawand, M. Berney, C. Brandt, P. H. Lambert, and C. A. Siegrist. 1996. Neonatal and early life immune responses to various forms of vaccine antigens qualitatively differ from adult responses: predominance of a Th2-biased pattern which persists after adult boosting. In *Eur J Immunol*, Vol. 26, p. 1489.
25. Barrios, C., C. Brandt, M. Berney, P. H. Lambert, and C. A. Siegrist. 1996. Partial correction of the TH2/TH1 imbalance in neonatal murine responses to vaccine antigens through selective adjuvant effects. In *Eur J Immunol*, Vol. 26, p. 2666.
26. Ridge, J. P., E. J. Fuchs, and P. Matzinger. 1996. Neonatal tolerance revisited: turning on newborn T cells with dendritic cells. In *Science*, Vol. 271, p. 1723.
27. Arnold, H., D. Bumann, M. Felies, B. Gewecke, M. Sorensen, J. E. Gessner, J. Freihorst, B. U. von Specht, and U. Baumann. 2004. Enhanced Immunogenicity in the Murine Airway Mucosa with an Attenuated Salmonella Live Vaccine Expressing OprF-OprI from *Pseudomonas aeruginosa*. In *Infect. Immun.*, Vol. 72, p. 6546.
28. Dhar, N., V. Rao, and A. K. Tyagi. 2003. Skewing of the Th1/Th2 responses in mice due to variation in the level of expression of an antigen in a recombinant BCG system. In *Immunol Lett*, Vol. 88, p. 175.
29. Etchart, N., B. Baaten, S. R. Andersen, L. Hyland, S. Y. Wong, and S. Hou. 2006. Intranasal immunisation with inactivated RSV and bacterial adjuvants induces mucosal protection and abrogates eosinophilia upon challenge. In *Eur J Immunol*, Vol. 36, p. 1136.
30. Marchant, A., T. Goetghebuer, M. O. Ota, I. Wolfe, S. J. Ceesay, D. De Groote, T. Corrah, S. Bennett, J. Wheeler, K. Huygen, P. Aaby, K. P. McAdam, and M. J. Newport. 1999. Newborns develop a Th1-type immune response to *Mycobacterium bovis* bacillus Calmette-Guerin vaccination. In *J Immunol*, Vol. 163, p. 2249.
31. Cirillo, J. D., C. K. Stover, B. R. Bloom, W. R. Jacobs, Jr., and R. G. Barletta. 1995. Bacterial vaccine vectors and bacillus Calmette-Guerin. In *Clin Infect Dis*, Vol. 20, p. 1001.
32. Fennelly, G. J., J. L. Flynn, V. ter Meulen, U. G. Liebert, and B. R. Bloom. 1995. Recombinant bacille Calmette-Guerin priming against measles. In *J Infect Dis*, Vol. 172, p. 698.
33. Hammerling, G. J., G. Schonrich, F. Momburg, N. Auphan, M. Malissen, Malissen, B, A. M. Schmitt-Verhulst, and B. Arnold. 1991. Non-deletional mechanisms of peripheral and central tolerance: studies with transgenic mice with tissue-specific expression of a foreign MHC class I antigen. [Review] [45 refs]. In *Immunological Reviews*, Vol. 122, p. 47.
34. Grange, J. M., J. Gibson, T. W. Osborn, C. H. Collins, and M. D. Yates. 1983. What is BCG? *Tubercle* 64:129.
35. Sambrook, J., E. F. Fritsch, and T. Maniatis. 1989. Molecular cloning. In *Cold Spring Harbor Laboratory Press*.
36. Kumar, D., B. S. Srivastava, and R. Srivastava. 1998. Genetic rearrangements leading to disruption of heterologous gene expression in mycobacteria: an observation with Escherichia coli beta-galactosidase in *Mycobacterium smegmatis* and its implication in vaccine development. In *Vaccine*, Vol. 16, p. 1212.
37. Stover, C. K., V. F. de la Cruz, T. R. Fuerst, J. E. Burlein, L. A. Benson, L. T. Bennett, G. P. Bansal, J. F. Young, M. H. Lee, G. F. Hatfull, and et al. 1991. New use of BCG for recombinant vaccines. In *Nature*, Vol. 351, p. 456.
38. Purkayastha, A., L. A. McCue, and K. A. McDonough. 2002. Identification of a *Mycobacterium tuberculosis* putative classical nitroreductase gene whose expression is coregulated with that of the acr aene within macrophages, in standing versus shaking cultures, and under low oxygen conditions. In *Infect Immun*, Vol. 70, p. 1518.
39. Yoon, Y. G., and M. D. Koob. 2005. Transformation of isolated mammalian mitochondria by bacterial conjugation. *Nucleic Acids Res* 33:e139.
40. Ahmed, S. U., M. Okamoto, T. Oshikawa, T. Tano, A. Sasai, S. Kan, T. Hiroshima, H. Ohue, Y. Moriya, Y. Ryoma, M. Saito, and M. Sato. 2004. Anti-tumor effect of an intratumoral administration of dendritic cells in combination with TS-1, an oral fluoropyrimidine anti-cancer drug, and OK-432, a streptococcal immunopotentiator: involvement of toll-like receptor 4. In *J Immunother*, Vol. 27, p. 432.

The invention claimed is:

1. An immunogenic formulation that confers protection against infection by a respiratory syncytial virus (RSV), and/or attenuates the pathology caused by an RSV, wherein the formulation comprises a recombinant attenuated *Mycobacterium* strain in an amount ranging from $10^4$ to $10^9$ bacteria (CFU/dose) per strain, wherein the recombinant attenuated *Mycobacterium* strain expresses at least one protein or immunogenic fragment thereof of the respiratory syncytial virus (RSV), in a pharmaceutically acceptable buffered saline solution.

2. The immunogenic formulation according to claim 1, wherein the recombinant attenuated *Mycobacterium* strain is derived from the Bacillus Calmette-Guerin (BCG) strain which expresses at least one protein or immunogenic fragment thereof of RSV.

3. The immunogenic formulation according to claim 1, wherein the respiratory syncytial virus is subtype A, B or both subtypes.

4. The immunogenic formulation according to claim 1, wherein the at least one respiratory viral protein or immunogenic fragment is a protein or immunogenic fragment thereof of protein NS1, NS2, N, P, M, SH, M2 (ORF1), M2 (ORF2), L, F or G of respiratory syncytial virus.

5. The immunogenic formulation according to claim 1, wherein nucleic acid encoding the at least one respiratory viral protein or immunogenic fragment is inserted into the genome of an attenuated *Mycobacterium* strain or is inserted into an extrachromosomal plasmid, in one or more copies, such that the viral protein or immunogenic fragment is expressed from the nucleic acid.

6. The immunogenic formulation according to claim 1, wherein the formulation comprises two or more strains of recombinant attenuated *Mycobacterium*, and wherein each of the strains expresses a different protein or immunogenic fragment selected from the NS1, NS2, N, P, M, SH, M2 (ORF1), M2 (ORF2), L, F or G proteins of RSV.

7. The immunogenic formulation according to claim 1, wherein the formulation comprises two or more strains of recombinant attenuated *Mycobacterium*, and wherein each of the strains expresses its RSV protein or immunogenic fragment in a different location, either as a soluble, soluble-cytoplasmic, extracellularly-secreted, or membrane-bound protein.

8. The immunogenic formulation of claim 1 wherein said formulation comprises two or more strains of recombinant attenuated *Mycobacterium*, and wherein the proteins or immunogenic fragments in the strains are expressed to generate a different number of copies, are expressed either constitutively or inducibly, and/or are located in different cellular locations.

9. The immunogenic formulation of claim 1 which is stabilized by freezing, freeze-drying or using a buffered saline solution for conservation prior to its use.

10. A method for protecting a subject against infection by or pathology caused by an RSV, comprising administering to the subject an immunogenic composition of claim 1.

11. The method of claim 10, wherein said formulation is administered by subcutaneous, percutaneous or subdermic administration.

12. The immunogenic formulation of claim 1, wherein the at least one respiratory viral protein or immunogenic fragment is a protein or immunogenic fragment thereof of proteins N and/or M2 (ORF1) of respiratory syncytial virus.

13. The immunogenic formulation according to claim 5, wherein the expression of the proteins or immunogenic fragments from the nucleic acid is controlled by constitutive or inducible, endogenous, or exogenous promoters of *Mycobacterium* BCG.

14. The immunogenic formulation according to claim 1, wherein the protein or immunogenic fragments are expressed as soluble cytoplasmic proteins, are secreted extracellularly, or are attached to the cell membrane.

15. The immunogenic formulation according to claim 1, wherein the formulation comprises two or more strains of recombinant attenuated *Mycobacterium*, and wherein each of the strains expresses a different protein or immunogenic fragment selected from the NS1, NS2, N, P, M, SH, M2 (ORF1), M2 (ORF2), L, F or G proteins of RSV.

16. A vaccine against RSV, comprising an immunogenic formulation of claim 1.

17. The vaccine of claim 16, which is formulated for subcutaneous, percutaneous, or subdermal administration.

18. The vaccine of claim 16, wherein the proteins or immunogenic fragments expressed are proteins N and M2 (ORF1) of RSV.

* * * * *

UNITED STATES PATENT AND TRADEMARK OFFICE
CERTIFICATE OF CORRECTION

PATENT NO. : 8,398,993 B2  
APPLICATION NO. : 12/679091  
DATED : March 19, 2013  
INVENTOR(S) : Kalergis et al.

Page 1 of 1

It is certified that error appears in the above-identified patent and that said Letters Patent is hereby corrected as shown below:

On the title page, item 73, Assignees should read: Pontificia Universidad Catolica de Chile, Santiago (CL), Bestpharma S.A. Quilicura, Santiago (CL)

Signed and Sealed this  
Twenty-fourth Day of September, 2013

Teresa Stanek Rea  
*Deputy Director of the United States Patent and Trademark Office*